United States Patent [19]
Menes

[11] Patent Number: 5,975,349
[45] Date of Patent: Nov. 2, 1999

[54] MICROSCOPE SLIDE DISPENSERS

[76] Inventor: Cesar M. Menes, 12905 E. Wolverton, Cerritos, Calif. 90701

[21] Appl. No.: 08/870,472

[22] Filed: Jun. 6, 1997

[51] Int. Cl.[6] .................................................. B65H 1/08
[52] U.S. Cl. ............................................ 221/232; 221/268
[58] Field of Search .................................. 221/232, 226, 221/268, 279, 272, 276, 255, 270

[56] References Cited

U.S. PATENT DOCUMENTS

| | | | |
|---|---|---|---|
| 3,152,722 | 10/1964 | Thomasma et al. | 221/232 |
| 3,393,831 | 7/1968 | Stewart | 221/232 |
| 4,240,564 | 12/1980 | Pritchard | 221/213 |
| 5,649,642 | 7/1997 | Mabry et al. | 221/232 |

Primary Examiner—Kenneth W. Noland
Attorney, Agent, or Firm—Natan Epstein; Beehler & Pavitt

[57] ABSTRACT

The invention provides a container for microscope slides incorporating an ejection device. In each of three disclosed embodiments the slides are ejected through an exit slot by manual actuation of an ejector so as to engage a rear of an end slide in a stack and push it forward through the exit slot. In each of the embodiments, the dispenser may be removably mounted on a base or holder. The holder may include a base plate with support arms. The slide dispenser may be factory sealed for clean or sterile slides and then be discarded or recycled when empty. Finally, the dispensing containers may be shrink wrapped at the factory to ensure sterility of the slides until needed.

34 Claims, 6 Drawing Sheets

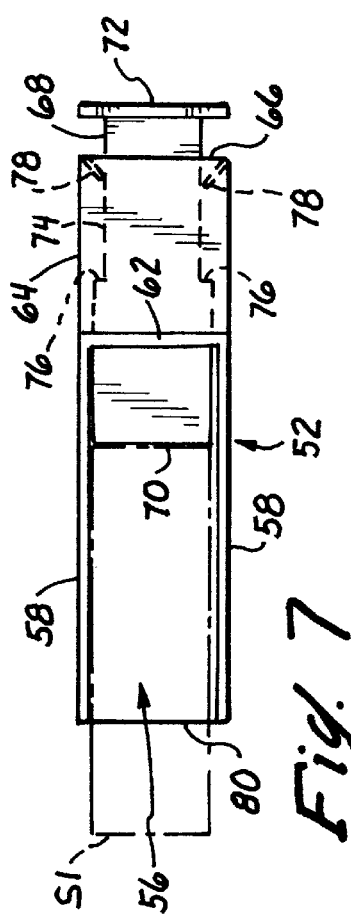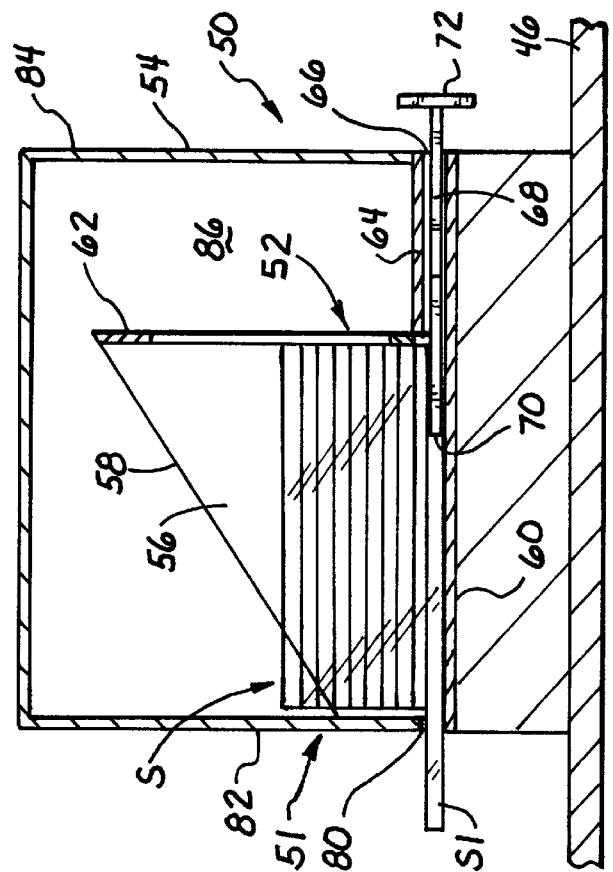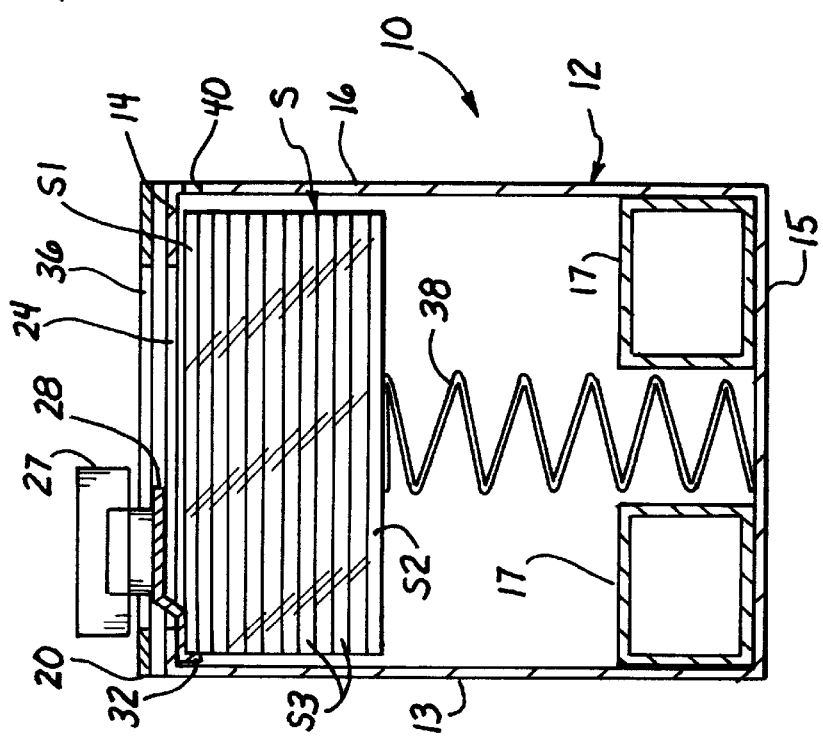

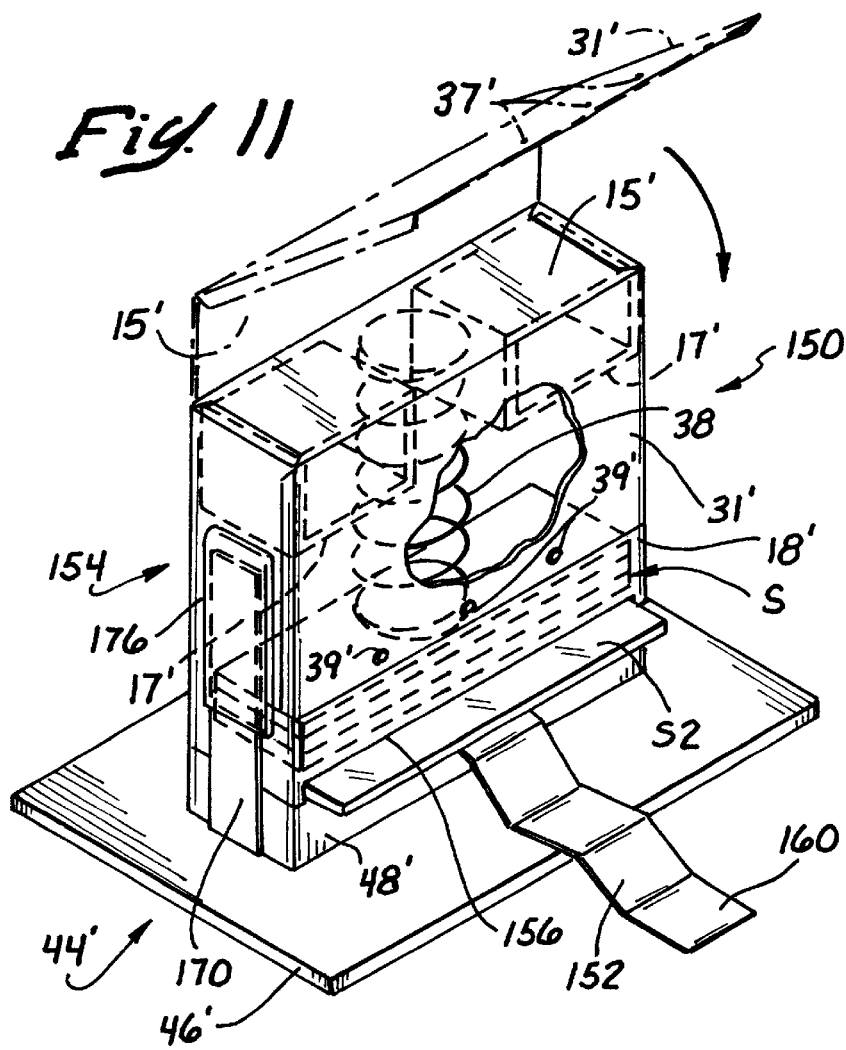
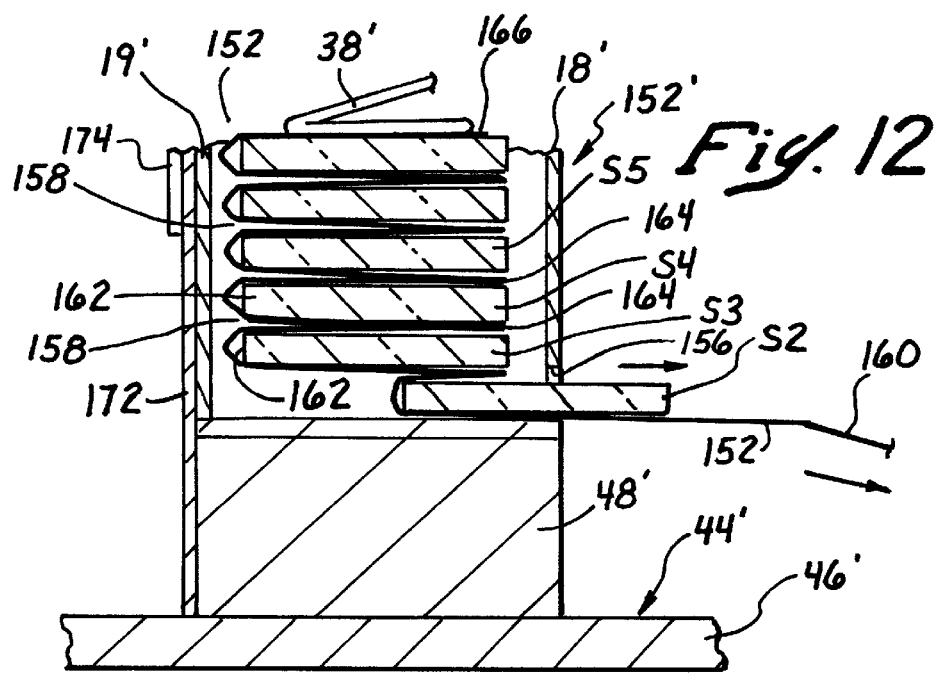

MICROSCOPE SLIDE DISPENSERS

BACKGROUND OF THE INVENTION

1. Field of the Invention

This invention relates to packaging and containers for microscope slides and to means for dispensing the slides from such containers.

2. Description of Prior Art

Microscope slides are well known as thin rectangular plates of glass on which fluid, tissue smears or other biological specimens may be mounted for examination under a microscope. These slides are manufactured by the millions and are generally sold in shallow cardboard boxes, in which the slides are placed on edge to form a horizontal stack filling the box bottom front to back, the longitudinal side edge of each slide lying on the bottom of the box (i.e., with the side of the stack laid onto the bottom surface of the box). A close-fitting top is then snugly fitted over the filled bottom, and the box is sealed in a wrapper to prevent contamination in transit to the end user.

While due care is usually taken by the manufacturer in preparing and packaging the slides, so that dust, fungal and bacterial spores, and other contaminants are prevented from readily adhering to them, once the box is open at, e.g. a laboratory site, removal of the slides by the end user is most often accomplished merely by grasping a slide and pulling it from the box. The slides are normally used one at a time and the open box with the stack of slides exposed to the laboratory environment is typically left on a table top until it is empty.

This practice leaves the unused slides in the open box exposed to contamination, for example by deposition thereon of aerosol droplets from sprays used in the laboratory, from medical specimen fluids themselves, and from various chemicals and liquids normally used in such laboratories, such as fixative compounds sprayed on specimens being prepared on other slides nearby, disinfectants, water sprays, etc., as well as dust and other airborne materials. Furthermore, even though slides are normally handled by the edges, it is difficult to avoid leaving finger marks in the form of deposited body oils and other substances carried on the fingers of laboratory personnel.

Not only does such handling of the slides promote their contamination—especially if the user's hand is not covered by a sterile glove—but it also subjects the laboratory personnel to the risk of cuts, as the user's fingers can easily slide along the sharp edges of the slides, when force is exerted to pull them from the box. This can happen because the smooth glass surfaces in a stack of slides adhere together rather easily when wetted by moisture or fluid droplets in an open box in the laboratory. As the technical personnel attempts to separate the slides skin cuts can occur rather easily. It should be noted that since economy is a key factor in the manufacture of microscope slides, the slide edges are normally not rounded or beveled, so that very little force is required to cause a finger cut to occur. Needless to say, skin cuts are undesirable in the septic environment of medical laboratories as infection may readily occur.

But because economy of production has been so important, and since packaging of microscope slides in such cardboard boxes has become so universal, little attention has been given to alternative packaging and dispensing. Also, since slides are normally grasped by the edges i.e., with a thumb and index finger placed at opposite sides of the longitudinal dimension of the slide (to remove it from the box) or the transverse direction (to mount the specimen and place the complete slide under the microscope)—it is assumed that little contamination occurs.

While such problems might be reasonably dealt with by careful training and supervision of professional laboratory technologists, these risks impose an additional burden on such personnel who already are under considerable strain because of the need to make careful evaluations of large numbers of medical specimens.

Thus, there is a definite need for some means by which microscope slides may be dispensed as needed from a protected container in a manner which minimizes the possibility of cuts and contamination.

Efforts have been made to solve—or, at least, to minimize—such difficulties by providing microscope slide dispensers which eject slides one at a time from within a protected enclosure. One such dispenser is illustrated in the 1992 Baxter Scientific Catalog as Catalog Number M6180, Manufacturer Nr. 1415, and is priced at US$157.60. This device which is made of sturdy sheet steel has a rectangular container into which a vertical stack of microscope slides can be introduced through a removable side panel such that the lowermost slide in the stack rests upon the bottom of the container. Built into a bottom compartment of the container is an ejection mechanism actuated by an external lever arm mounted on one side of the slide container. Manually depressing the lever arm through an angle of approximately ninety degrees advances an ejector element under the lowermost slide in the stack. The ejector element has an upstanding lip which engages a rear edge of the lowermost slide and pushes the opposite end of the slide through a slot in the side of the container. The protruding end of the slide can then be manually grasped and the rest of the slide pulled from the dispenser. The next lowermost slide then drops to the bottom into position for ejection when the lever is again actuated. While this existing device works well, the actuating lever is spring loaded and its design calls for rugged construction in order to withstand the repeated compression of its internal spring element, and therefore the device is fabricated of steel. While durable and reliable, this device is expensive, and consequently its widespread use—when measured against the typical process of removing slides by hand, one-by-one, from an open cardboard box—has been limited. And, in any event, the entire stack of slides must be still initially be removed from its original cardboard box by hand and then hand-loaded into the dispenser, so that opportunity for contamination still exists.

In another existing microscope slide dispenser the lowermost slide in a stack rests upon a cylinder which can be turned by means of an external knob, ejecting the lowermost slide sideways and edgewise from the stack through a slot in the housing containing the stack as a result of frictional force between the bottom slide and the rotating cylinder surface. This dispensing device has been found to be somewhat unreliable as the cylinder surface wears and diminishes in friction through usage, until it tends to merely slips against the bottom slide in the stack. Again, this dispenser too must be hand loaded with slides taken from a factory package.

What is needed is a simple, less expensive device in which microscope slides may be packaged—or into which they may be easily inserted—and from which they may be removed individually, with minimized susceptibility to contamination of the slide surfaces and a relatively smaller likelihood of finger cuts. In particular a need exists for a slide dispenser which is of sufficiently low cost as to be suitable for use as the original factory packaging for the slides, thereby eliminating the need to transfer the slides to a separate dispenser at a laboratory or other end user location. Optimally, the slide dispenser should be of sufficient simplicity and low cost as to be discardable or recyclable after a single use, so that factory packaged slides may be dispensed one at a time for immediate use in the laboratory, with no intermediate handling or exposure of the slides.

BRIEF SUMMARY OF THE INVENTION

In order to meet the aforementioned need, this invention provides a container for microscope slides, which may be disposable, incorporating an ejection device by which individual slides, held within the container, may be selectively ejected therefrom. The means by which the slides are held within, and ejected from, the container, and the configuration of the slide container itself, vary among the several principal embodiments of the invention described below. In all cases however, the slide ejection means are of simple yet reliable construction and, unlike some of the above described existing slide dispensers, do not require use of high strength, and therefore costly, materials in order to achieve dependability.

In each of three disclosed embodiments of the invention the slides are ejected through an exit slot in the container by manual actuation of a linearly displaceable ejector disposed and configured so as to engage a rear or trailing edge of an end slide in the stack and push its opposite forward or leading edge through the exit slot. The action of the ejector is simple yet positive. The ejector is shown in different forms: in one form it has a tab projecting vertically through an access slot in a top of the container, the ejector travels between the leading and trailing edges of the slides in the container, and has a slide abutment or catch element arranged for engaging the trailing edge of the slide to be dispensed from the container. In another form of the invention, the ejector extends through an access slot in a side wall of the container opposite to the exit slot. In both these forms the ejector has a portion internal to the dispensing container with a slide abutment which engages the slide to be ejected when the exterior portion of the ejector is manually operated in the appropriate fashion. In both cases the ejector may be a simple assembly with no moving parts or a unitary element, and is subject only to the modest manual forces needed to push an end slide from the stack through the exit slot. The great simplicity of the ejection mechanism, yet without compromise in reliability, permits the microscope slide dispensers disclosed herein to be manufactured in large quantities of low cost materials, for example by injection molding of a suitable commercially available plastics. These slide dispenser may be advantageously used as factory sealed original packaging for clean or sterile microscope slides, and then be discarded or recycled when empty, thereby eliminating all handling of the microscope slides and their exposure to possible contamination until such time as each slide is individually removed from the container for immediate use. The dispensing containers of this invention may be shrink wrapped or otherwise sealed at the factory in an impermeable film to ensure cleanliness or sterility of the slides until needed at the end user location. The containers may also be locked closed when filled at the factory or other wholesale distribution point, to discourage or prevent refilling and reuse of the dispensers in the interest of encouraging use of only factory or distributor packaged microscope slides of reliable cleanliness.

In a first embodiment, a spring urges a stack of slides against a top within the container. An exit slot in a side wall of the container near the top is dimensioned for passing only an individual slide at one time. A cap over the top of the container has an access slot, oriented along the longitudinal direction of the slides held within the container. An ejector assembly includes a portion slidably captive between the cap and the top of the container with an attached finger tab which extends through the access slit. The ejector assembly also has a catch or slide abutment which projects downwardly into the container through an access opening in the top of the container. The ejector assembly is arranged such that in a retracted position of the ejector, the catch is located behind the rear edge of the topmost slide in the stack. When the finger tab is manually slid forward, toward the exit slot, the catch pulls the topmost slide forward and through the exit slot, from which it may be removed gently and easily, without undue danger of a finger cut. Return of the finger tab to the retracted position allows a second slide in the stack to be pushed upward, into topmost position and into engagement by the catch of the ejector, which slide may also be slid outward through the exit slot when the finger tab along with the ejector assembly is again slid to a forward position.

In a second embodiment, ejection of the slides occurs at the bottom of the container. A stack of slides is held within the container such that the lowermost slide rests upon the bottom of the container, with one end facing an exit slot and the other end facing an access slot. The exit slot is dimensioned to allow the slide to pass there through, while the access slot is dimensioned to allow sliding passage of an elongated ejector element. An interior end of the ejector element abuts the rear edge of the lowermost slide in the stack, while the opposite exterior end of the ejector element terminates in an enlarged stop or finger plate. The stop is dimensioned so that it will not slide through the access slot into the container, and to provide a somewhat enlarged surface against which the user's finger may be applied. The microscope slides in the stack may be gravity fed towards the ejector element and exit slot at the bottom of the container.

A third embodiment somewhat resembles the aforementioned second embodiment, except that in this third embodiment, a side of the container which faces one longitudinal side edge of each slide in the stack is hinged to the container, and has clasps by which it may be secured into a closed position against the container. When these clasps are snapped into place, the container is closed. When they are released, and the hinged side is swung away from the rest of the container, the container is opened. A stack of slides may be inserted therein simply by laying the container onto its closed far side, opening a conventional cardboard box of slides and tipping the box over onto the open side of the container, thus dropping the stack of slides into the container. Slides may similarly be removed from the container by opening its side and tipping out the stack of slides held within. Neither operation need involve hand contact with any of the slides in the stack. In this embodiment, the entire container may be configured as a one-piece structure, into which a stack of slides may easily be inserted by the manufacturer (or user) and which may then be snapped shut. As in the aforementioned second embodiment, a rigid ejector element slides in an access slot against a rear edge of the lowermost slide in the stack, so that individual slides may be selectively ejected from the exit slot by pushing the exterior end of the ejection finger.

A fourth embodiment differs from the previous three embodiments in that the slidable ejector is replaced by a continuous flexible pull tape folded and interlaced with the slides in the stack. The pull tape is folded in accordion fashion and interlaced with the slides such that each slide is contained within a fold of the pull tape. Within the container, the slides and exit slot are mutually oriented so that as the pull tape is selectively withdrawn and unfolded through the exit slot, individual slides are withdrawn edgewise through the exit slot, preferably with a long edge first through the exit slot.

In order to provide stability and convenience while slides are being ejected from the container, in each of the second, third and fourth of the aforementioned four embodiments, the dispenser of this invention may be removably mounted on a supporting base or holder, which optionally may be firmly secured to a table or other rigid structure. This holder may include a base plate with upwardly projecting support arms. The latter are positioned and dimensioned so that corresponding sleeves on the dispenser container may be slid downward over them. When so mated to the holder the container is held securely on the base while slides are dispensed therefrom.

Various of the disclosed embodiments also feature side loading of the stack of slides through a movable side of the slide container, admitting the stack of slides in a sideways direction into the container between the spring and the exit slot of the container, facilitating loading of the slides over conventional slide dispensers which are top or bottom loading. The ejector slide of the dispenser is sized and configured for urging at least one third of the length of each slide through the exit slot for easy grasping and removal by a user.

These and other features, advantages and improvements will be better understood by reference to the following detailed description of the preferred embodiments, wherein like elements are designated by like numerals in the accompanying drawings.

BRIEF DESCRIPTION OF THE DRAWINGS

FIG. 4 is a cutaway side elevation view of the invention shown in FIG. 1, taken through section line 4—4 in FIG. 1;

FIG. 6 is a cutaway side elevation view of the invention shown in FIG. 5, taken through section line 6—6 in FIG. 5;

FIG. 7 is a partial cutaway plan view of the invention shown in FIG. 5, taken through section line 7—7 in FIG. 5;

FIG. 11 is an isometric view of the invention according to the fourth embodiment thereof;

FIG. 12 is a elevational sectional view of the lower portion of the dispenser shown in FIG. 11.

DETAILED DESCRIPTION OF THE PREFERRED EMBODIMENTS

Figure 1:
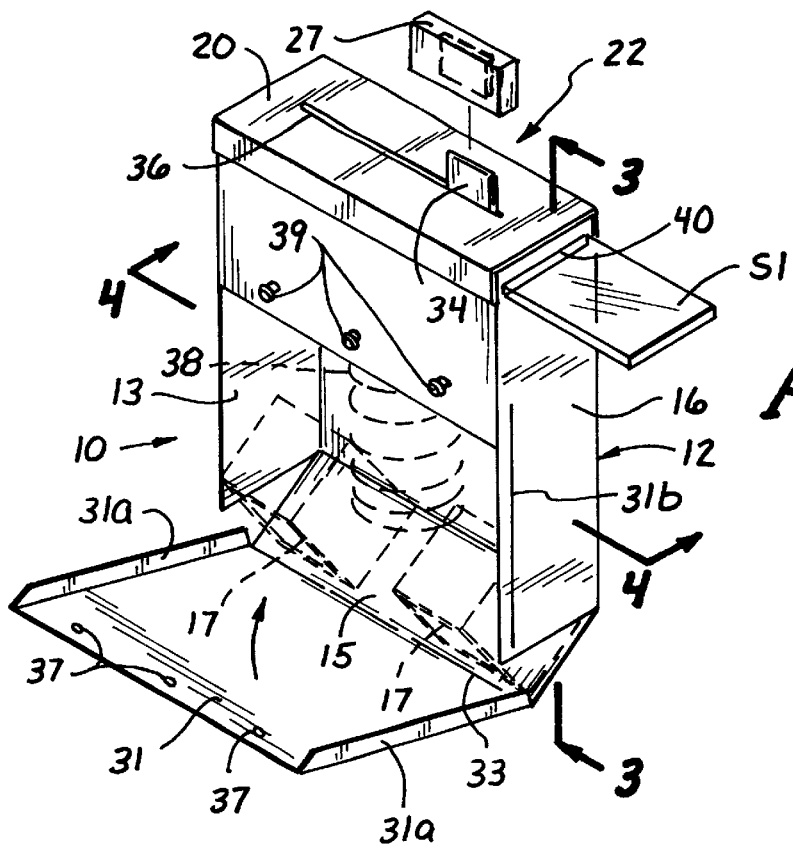
FIG. 1 is an isometric view of the microscope slide dispenser of this invention according to a first embodiment thereof.
Figure 2:
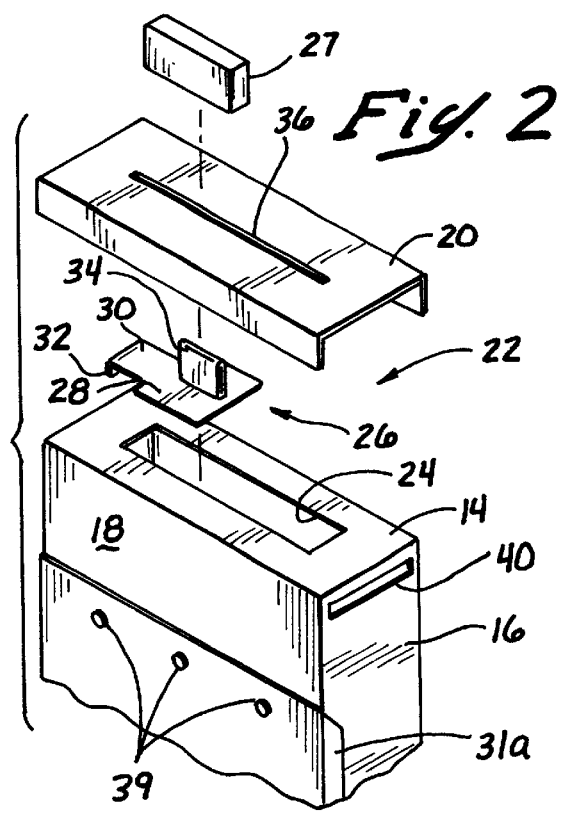
FIG. 2 is an exploded isometric view of the upper portion of the dispenser shown in FIG. 1.
Figure 3:
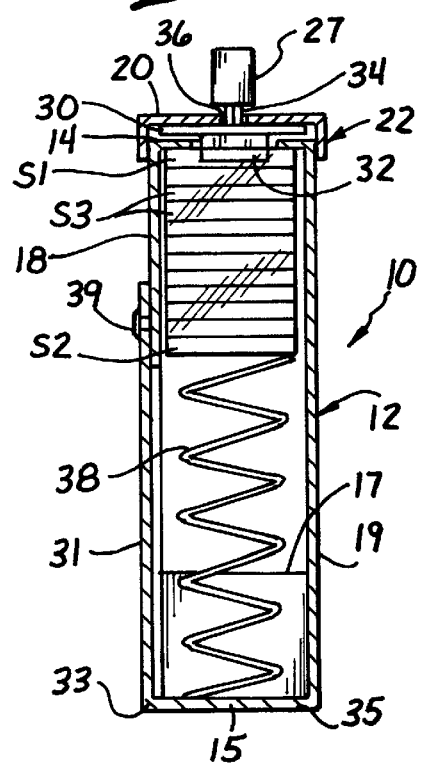
FIG. 3 is a cutaway end elevation view of the invention shown in FIG. 1, taken through section line 3—3 in FIG. 1.

With reference to the accompanying drawings, FIGS. 1–4 show a first embodiment of the microscope slide dispenser according to the invention, generally designated by the numeral 10, and which is seen to have a microscope slide housing or container 12 of generally rectangular shape and which has a top 14, a top cap 20 fitted over the top 14, a front side 16, a rear side 13, a left side 17 and a right side 18. An elongated rectangular access opening 24 in the top 14. An ejector 26 has a rectangular plate 28, a narrower ejector finger 30, bent to form a downward projecting lip 32, and a finger tab 34 which rises vertically from the plate 28 through an access slit 36 cut in the cap 20. The width of the ejector finger 30 and the lip 32 fits closely in the width of the access opening 24, while the plate 28 is wider than the opening 24 and rests on the top 14 of the container. The cap 20 captures the ejector plate 28 against the top 14. However, the ejector 26 remains free to slide linearly back and forth along the length of the opening 24 and the slit 36, between a retracted position indicated in FIG. 4 and a forward position shown in FIG. 1. An enlarged finger cap 27 may be fitted over the finger tab 34 for easier manipulation.

The container 12 is internally-dimensioned for holding a vertical stack S of microscope glass slides in predetermined relationship to the ejector 26, with the long dimension of the slides aligned with the direction of movement of the ejector. The stack of slides, generally designated by the letter "S" includes a top end slide S1, a bottom end slide S2, and one or more intermediate slides, S3. A coil spring 38, shown in phantom lining for clarity of illustration, is compressed between a bottom 15 of the container 12, and the under surface of the bottom end slide S2, lifting the stack S against the top 14 of the container. An exit slot 40 is defined in the front side 16 of the container adjacent to the top 14. The exit slot is aligned with a leading edge of the top end slide S1 in the stack S. The lip 32 of the ejector 26 is a slide abutment or catch which, in the retracted position of the ejector 26, engages the trailing or rear edge of the top end slide S1. Manually advancing the ejector 26 to its forward position advances the top end slide S1 toward and partially through the exit slot 40, as illustrated in FIG. 1. As also shown in FIG. 1, the ejector 26 is effective for advancing at least one third of the length of the top end slide through the exit slot 40, to provide a substantial exposed length of the slide which can be comfortably grasped along its edges by a user, and easily pulled from the dispenser unit.

Access to the interior of container 12 is gained by opening a side cover 31, shown open in FIG. 1, which is connected along its lower edge 33 to the bottom 15 of the container. Bottom 15 is hinged along edge 35 to the lower edge of the left side 19 of the container, as best understood from FIGS. 1 and 3. The spring 38 is readily removed from the container for loading a stack S of slides against the top 14. The spring 38 is then reinstalled between spring centering blocks 17 by compression between the bottom 15 and the underside of the bottom end slide in the stack S, thereby urging the stack towards the exit slot and supporting the stack against the top 14 under continuous spring force. As will be understood from FIG. 1, the stack S of slides is loaded through the open side of container 12 in a sideways direction, i.e. with the edges of the individual slides advancing through the open side into the container 12, rather than along the height of the stack. This is a more advantageous mode of loading the slides into container 12 because, as mentioned above in the introductory portion of this specification, slide vendors customarily package microscope slides in shallow cardboard boxes or trays with the slides lying on their edges. Consequently, the side loading feature of the novel slide dispenser permits the stack of slides to be lifted from their original box and inserted with a minimum of manipulation into the open container 12. This is considerably easier to do than loading conventional loading slide dispensers where the stack of slides must be inserted upwards or downwards along its height into the dispenser's magazine. Preferably, the centering blocks 17 and the bottom 15 are made as one piece. The side cover 31 is secured in its closed condition to the right side 18 of the container by means of three fasteners 39 which make retentive engagement through corresponding holes 37 in the side cover. The fasteners or retainers 39 may be of a conventional design, either of a type which readily releases the side cover 31 to permit reloading of the dispenser 10, or of a type which expands once inserted through the holes 37 and is thereafter difficult to release, in order to discourage refilling of the container 12 once an original supply of factory loaded slides has been exhausted. The fasteners 39 may be integral to the container 12, for example formed therewith by injection molding of plastic in order to minimize parts count and assembly. The side cover 31 also has two side flanges 31a normal to the side cover 31 and which fit snugly over the front and rear sides 16, 13 respectively of the container 12 to help secure the side cover in place. The side flanges may also fit into slits 31b to further secure the side cover.

The cap 20, ejector 26, the apertured top 14 of the housing 12 and exit slot 40 together constitute a simple, reliable slide ejection assembly 22 with no pivoted or rotary components, and in which none of the components are subject to heavy loads or high stresses, either in its static condition or during its operation. As a result, all elements of the slide dispensing assembly 22 can be made of low cost materials such as plastics or thin sheet metal, such as thin aluminum sheet metal, with no adverse impact on the performance of the slide dispenser. This in turn permits the slide dispenser assembly 22 to be integrated in the manner just described to a package such as the container 12, for use as factory original packaging filled with sterile or otherwise clean microscope slides at the site of manufacture or wholesale distribution. The container 12 with integral slide dispenser 22 may be discarded once all the slides in the stack S have been used up and the container is empty. The simple, low cost design and construction of the integral slide dispenser 22 assembly therefore eliminates the need for handling of the slides at any point between original packaging and the subsequent removal of individual slides from the container 12 at an end user location only when actually required for immediate use. Furthermore, the opportunity for contamination by exposure of the slides at any intermediate point between the original packaging and use is also eliminated.

Within the closed container 12 the microscope slides are fully enclosed and protected against exposure to possible contaminants in the immediate environment. For greater protection the top cap 20 may be partially or entirely made of a resilient material such that the slit 36 tends to close shut around the finger tab 34 to provide a seal over the access opening 24.

The slide dispenser of FIGS. 1–4 can be conveniently carried in a pocket and used in a handheld manner. This is a particular convenience for medical personnel such as pathologists who are called upon to take medical laboratory samples and specimens at different locations dispersed throughout a medical facility, where a box of microscope slides is not always at hand. With such use in mind the dispenser is designed to operate in any relative position, whether upright, inclined or inverted, and is not dependent on gravitational force for its operation. Furthermore, the slides are conveniently dispensed from an upper end of the container 12 while the lower parts of the container are held in one hand and the other hand of the user operates the slide ejector 26.

Figure 5:
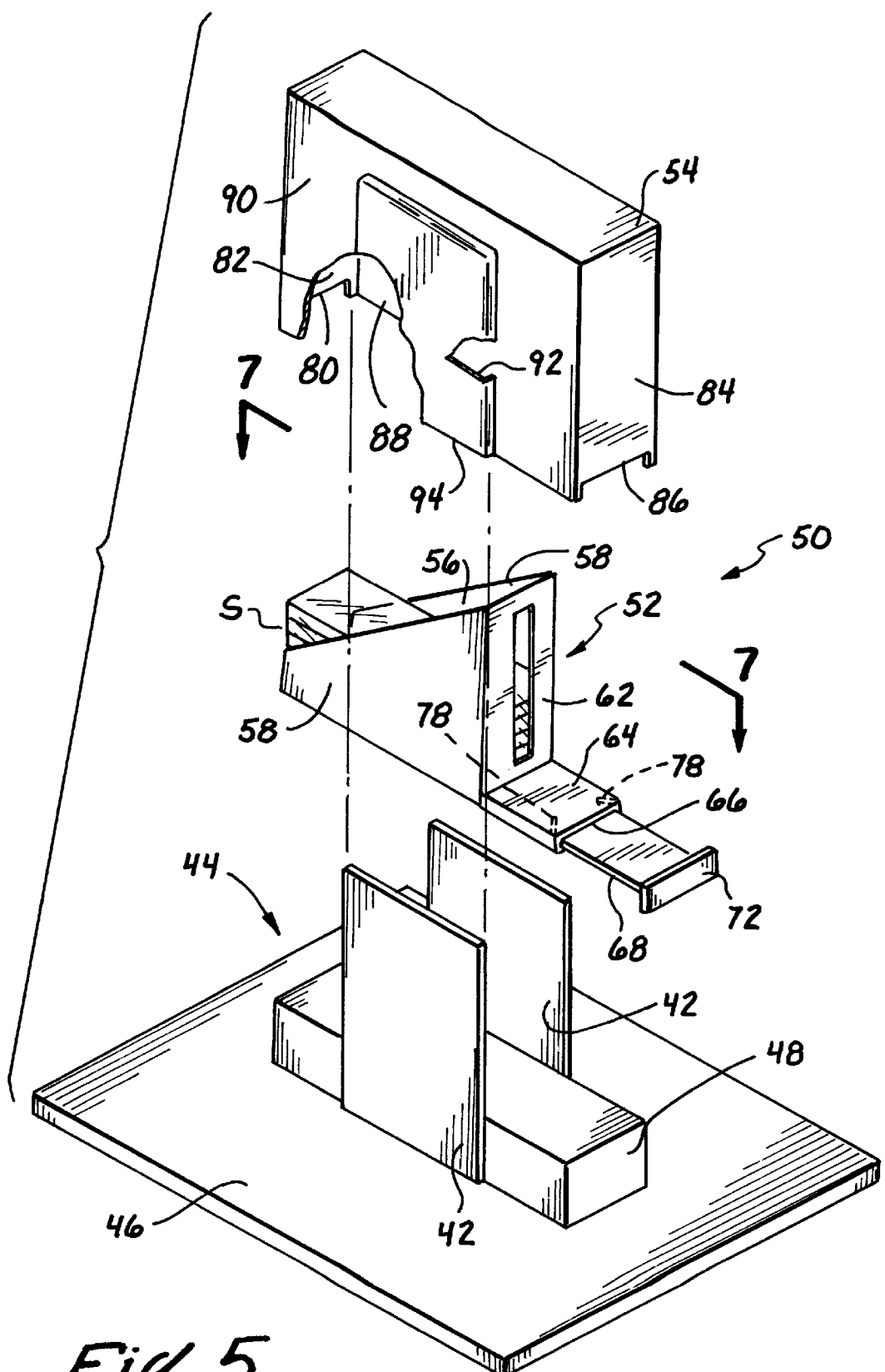
FIG. 5 is an exploded, partially cutaway, isometric view of the invention according to the second embodiment thereof.

An optional holder generally designated by the numeral 44 in FIGS. 5 and 6 has a relatively large rectangular base plate 46, a support block 48 affixed to the center of the base plate 46, and a pair of arms 42 affixed to opposite sides of the block 48. The right and the left sides, 88 and 90 respectively, of the container 12 each carry an exterior sleeve of which only the left sleeve 92 is seen in FIG. 5, and which are open at a lower end 94 and closely receive the upwardly extending arms 42 of the holder 44 when the slide dispenser 50 is slid downwardly between the arms 42.

A second embodiment, generally designated by the numeral 50, of the microscope slide dispenser according to this invention is depicted in FIGS. 5 through 7 of the drawings. In the second embodiment the microscope slides are gravity fed to a slide ejection assembly disposed at the bottom of the slide container 51. The container 51 includes a lower assembly 52 and a cover 54. The lower assembly includes a magazine 56 defined by two side walls 58, a bottom 60 and a rear wall 62. A vertical stack S of slides is contained in the magazine 56.

Turning to FIG. 6, it is seen that the lower assembly 52 has an ejector sleeve 64 which extends rearwardly from the rear wall 62, and terminates in an access slot 66. An ejector 68 is linearly slidable within the ejector sleeve 64, and has a forward slide abutment edge 70 interior to the container and a finger plate or end plate 72 attached to its opposite end outside the access slot 66, as best shown in FIGS. 6 and 7. The ejector 68 is a flat, planar plunger of thickness equal or lesser than the thickness of slides in stack S, and has a rear portion of reduced width 74, which defines shoulders 76. Retaining tabs 78, which may be formed integrally with the ejector sleeve, are bent into the access slot 66 and are resiliently flexible such that they spread apart to admit installation of the wide inner or front portion of the slide ejector 68 into the sleeve 64 during initial assembly of the dispenser 50. Thereafter however, the retaining tabs 78 abut against the shoulders 76 in a maximally retracted condition of the ejector and prevent the ejector from being fully withdrawn and separated from the lower assembly 52. This design makes for easy assembly of the dispenser with a minimum of parts.

When fully retracted into the ejector sleeve 64, the forward abutment edge 70 of the ejector is withdrawn from underneath the stack S and into the ejector sleeve 64, thereby to permit the bottom end slide S1 to drop onto the bottom 62 of the magazine 56, such that the rear or trailing edge of the bottom end slide S1 is aligned with the abutment edge 70 of the ejector plunger.

Ejection of the bottom end slide S1 is achieved by manually advancing the ejection plunger 68 into the magazine and towards exit slot 80 defined in the front side 82 of the cover portion. The rear side 84 of the cover portion has a cut out 86 provides clearance for the end of the ejector sleeve 64 and access slot 66. An internal clearance space 86 exists between the rear wall 62 of the magazine 56 and the rear side 84 of the cover 54. This clearance space 86 accommodates the length of the ejector sleeve 64 and provides a space into which the abutment edge 70 at the inner end of the ejector plunger 68 an ejection plunger may be retracted in order to permit the bottom end slide S1 to drop into position for ejection, after a previous bottom end slide has been ejected from the stack S. The ejector plunger 68 operates to push each bottom end slide S1 partially through the exit slot 80, to a position such as indicted in phantom lining in FIG. 7 and in solid lining in FIG. 6. Once in that partially ejected position, the bottom end slide can be easily removed by the user who simply grasps the side edges of the slide and pulls the remaining length of the slide from the dispenser unit 50.

Figure 9:
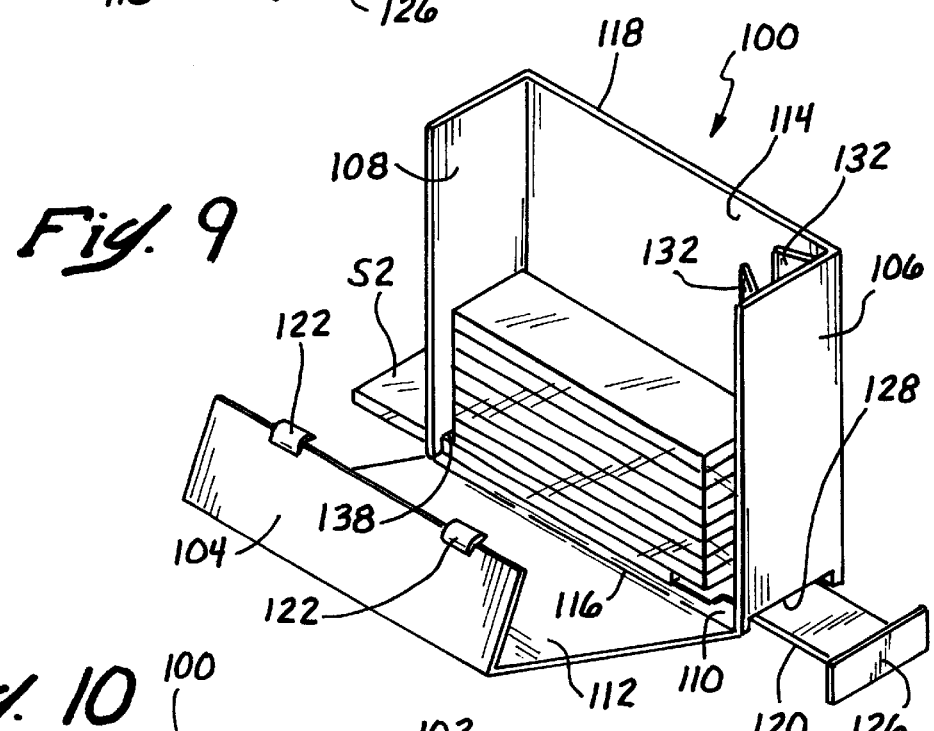
FIG. 9 is an isometric view of the dispenser of FIG. 8, wherein the container is shown in the open configuration.
Figure 10:
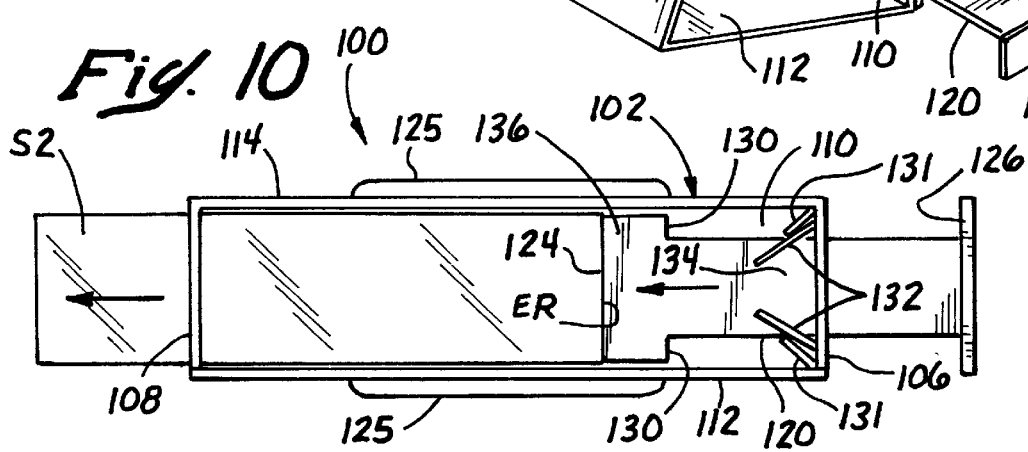
FIG. 10 is a cutaway top plan view of the dispenser of FIG. 8.

A third embodiment of the dispenser according to this invention is illustrated in FIGS. 10 through 12. This third embodiment, generally designated by numeral 100, resembles the second embodiment of FIGS. 5 through 7 in that the slide ejection mechanism is at the bottom of a rectangular slide container 102, which has a top 104, a front side 106, rear side 108, a bottom 110, a left side 112 and a right side 114. The left side 112 has a lower edge 116 which is hinged to the bottom 110, for movement between the closed position shown in FIGS. 8 and 10 and the open position illustrated in FIG. 9. The top 104 of the container 102 carries a pair of snap retainers 122 which engage the top edge 118 of the right side 114 in the closed position of FIG. 10, to secure the container 102 in its closed condition.

The left side 112 and the top 104 together form a hinged side cover of the container, such that in the open condition of the container 102, the entire interior of the container is fully exposed and accessible for loading of a stack S of microscope slides quickly and easily. An entire stack of slides can be dropped into the open container 102, and the side cover may then be snapped shut, making the dispenser 100 ready for dispensing of individual slides from the stack S. Ejection of the individual slides is accomplished by means of an ejector plunger 120, which operates generally as described in connection with the plunger 68 in the second embodiment of FIGS. 5–7. The plunger 120 has a forward slide abutment edge 124 interior to the container 102, and a finger rest or end plate 126 attached to the exterior end of the ejector plunger. The plunger 120 also has a portion of reduced width 126 which is slidable through an access opening 128 in the rear side 106 adjacent to the bottom 110. Retraction of the plunger from the container is limited by abutment of shoulders 130 on the plunger which are stopped by the inwardly bent detent tabs 131 which are analogous to detent tabs 78 of the previously described embodiment. In this position, the abutment edge 124 is withdrawn from under the stack S of microscope slides and lies underneath a pair of vertically extending spacer vanes 132 which extend from the interior surface of the rear side 106 towards the stack S of slides in order to space the slides from the rear side 106. In this fully retracted condition, the ejector 126 permits the bottom end slide S1 to rest upon the bottom 110 of the container 102 in alignment with the plane of the ejector plunger 126, such that the abutment edge 124 of the ejector plunger is aligned with a trailing rear edge ER of the bottom end slide S2. The spacer vanes 136 define an interior space 134 into which the forward end 136 of the ejector plunger can be withdrawn to permit the stack S to successively drop under the influence of gravity onto the bottom 110, as each successive bottom end slide in the stack S is ejected in turn. Ejection occurs by manually advancing the ejector plunger 126 into the container 102, thereby pushing the forward abutment edge 124 against the trailing edge ER of the bottom end slide S2 which is thus pushed through an exit slot 138 defined near the bottom end of the front side 108, opposite to the access slot 128, as suggested by the arrows in FIG. 10. The bottom end slide S2 is partially pushed through the exit slot 138 and the protruding portion of the slide S2 can then be grasped by the user and pulled out of the container 92 for immediate use without exposing the remaining slides in the stack S to either manipulation or contamination.

The housing 102 is shown equipped with side sleeves 125 which are structurally and functionally equivalent to sleeves 92 in the previously described dispenser 50, for securing the dispenser 100 to a holder such as holder 44 in FIG. 5.

It will be appreciated that in the second and third embodiments just described there is little opportunity for the slides in the containers to be exposed to contamination, as the main surfaces of the microscope slides are well protected even against the small likelihood of entry of contaminants through the exit slot and access slot of the respective containers.

In each of the three embodiments described above, the slide ejector is a simple device which moves only in linear fashion and is easily and simply reciprocated between a retracted and advanced position by manually pushing and pulling the ejector relative to the microscope slide container. In none of the embodiments is the ejector subjected to substantial torque or to large resilient forces or spring loading, and even the frictional resistance encountered by the ejector mechanism is quite low, as the microscope slides are very smooth surfaced and tend to slide easily against each other and against the interior surfaces of the container. In each embodiment, all parts of the dispenser assembly including the ejector and the microscope slide container can be made of low cost injection moldable, recyclable thermoplastic as a single use disposable microscope slide package with integral slide dispenser.

Figure 8:
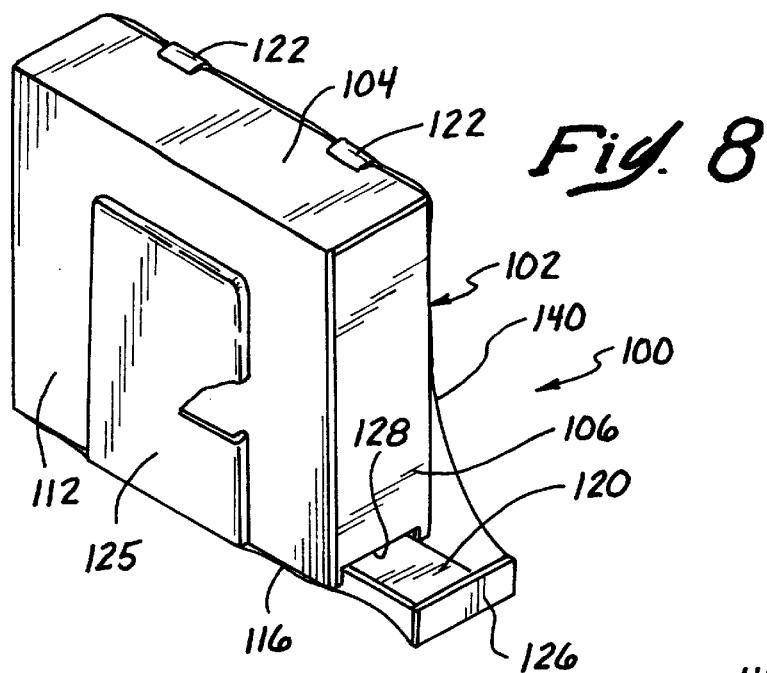
FIG. 8 is an isometric view of the fully assembled, closed dispenser of the invention according to the third embodiment thereof.

In each of the embodiments described, the slide dispenser can be sealed in a suitable, impermeable outer wrapper, such as a shrink wrap film, as exemplified by shrink wrapper 140 in FIG. 8, where the wrapper film completely encloses the container 102 as well as the exterior portion of the ejector plunger 120, sealing both the exit slot 138 and access slot 128 of the container. The seal wrapper 140 is normally removed only at the end user location, just prior to use of slides in the container. The slides are thus protected against all exposure and handling from the time that the container 102 is filled at the factory or wholesale distribution facility until such time as the slides are to be put to immediate use at an end user location.

Figure 13:
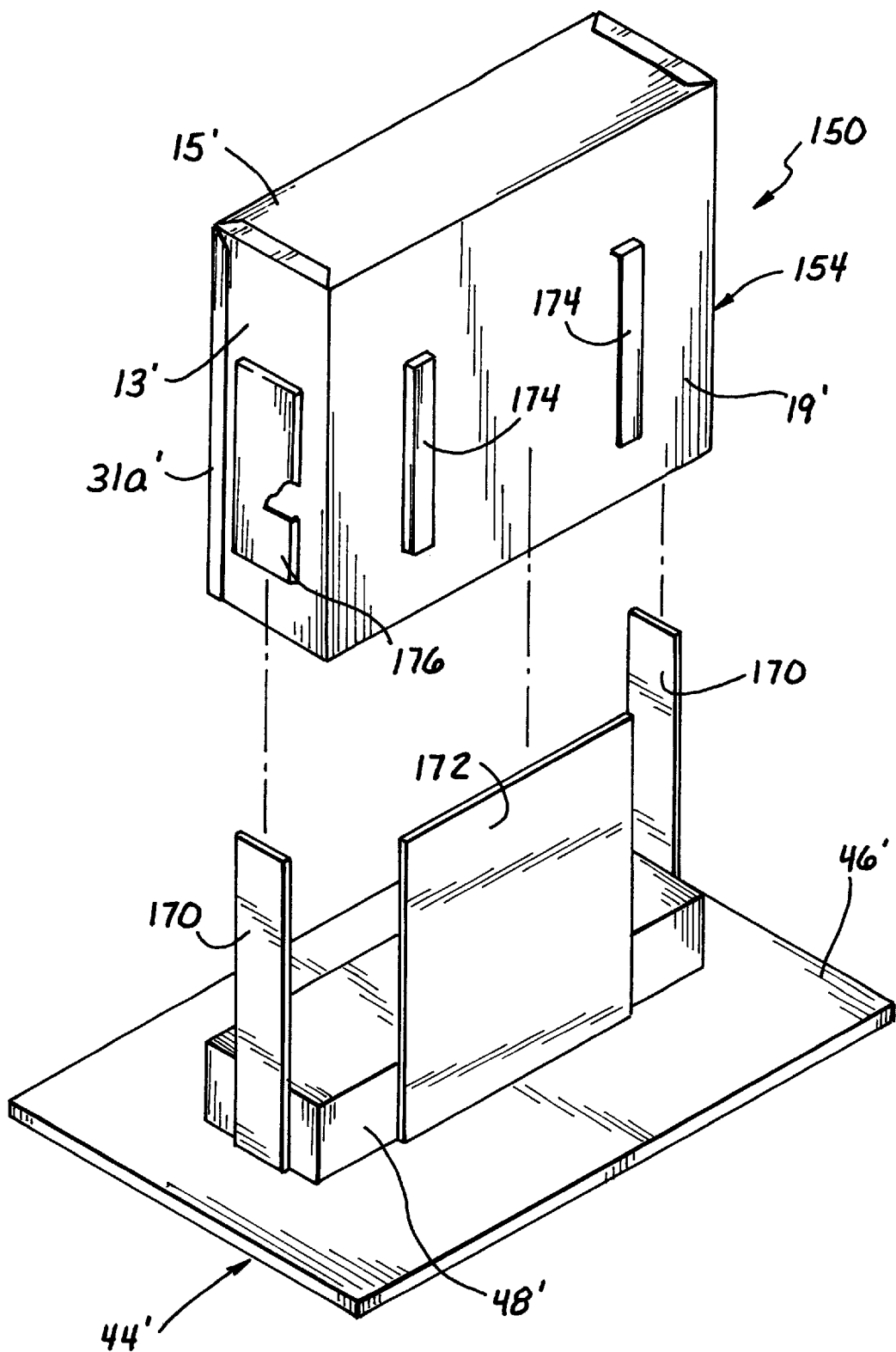
FIG. 13 is a rear isometric view of the dispenser of FIG. 11 in exploded relationship with a supporting base or holder.

The fourth of the four disclosed embodiments of the invention, generally designated by numeral 150, is illustrated in FIGS. 11–13, and differs from the previously described three embodiments, principally in that the linearly slidable ejector of the previous embodiments is replaced by a pull tape 152. The dispenser 150 has a container generally designated by numeral 154 which in its basic construction is similar to the container 12 of FIGS. 1–4, except that the slide ejection assembly 22 has been eliminated, and the container 154 is mounted on a holder 44' in inverted relationship to the position of the container 12 in FIGS. 1–4. Elements in container 150 are designated with primed numerals similar to the unprimed numerals designating equivalent elements in container 12. The construction and function of the elements indicated by primed numerals in FIGS. 11–13 will be readily understood by reference to the earlier description of the equivalent elements in FIGS. 1–4.

In the slide dispenser 150 the microscope slides s2, s3, etc., are withdrawn individually through the exit slot 156 by pulling on tape 152 which is folded in accordion fashion to make successive V-folds 158, with each microscope slide contained between successive V-folds 158 of the tape in the manner shown in FIG. 12. For purposes of further discussion, the configuration of the tape 152 when the slides s2, s3, etc., are held within it will be referred to as being "interlaced" with the slides, where such "interlacing" is as shown in FIG. 12. More specifically, the tape 152 is interlaced about the lowermost two slides s2, s3 in the following zigzag manner: a free end 160 of the tape 152 is exterior to the container 154. From the free end the tape passes through the exit slot 156 into the container under the bottom end slide S2 to the back edge 162 of that slide. The tape then is folded over the top of slide S2 and passes towards the front edge 162 of slide S2 where the tape is folded over itself in a sharp V-fold 158 along a fold edge 164, and then returns towards the back edge 162 of the next slide S3, where the tape again wraps over the back edge 162 and is then again folded into a V-fold 158 between slides S3 and S4. This pattern is repeated for each adjacent pair of slides in the stack S. Thus, the tape 154 interlaces the entire stack S of microscope slides within the container 152. The slides can be withdrawn or ejected from the container 152, one by one, by simply pulling on the exterior free end 160 of the tape 152. Pulling on the tape has the effect of urging the rear edge 162 of the bottom end slide S2 towards the exit slot 156, until the entire width of that slide is withdrawn through the exit slot. At that point, the bottom layer of the first V-fold 158 has been pulled out through the exit slot along with the slide as will be understood by reference to FIG. 12, and further pulling on the tape begins to urge the rear edge 162 of the next slide, S3, which is now the new bottom end slide in the stack S, towards the exit slot. This process is repeated each time that a slide is removed from the container, until the stack S has been exhausted and the container 154 is empty of slides.

Spring 38' compressed between the top 15' of the container 154 and the top end slide S1 of the stack S with the top end 166 of the tape captive between the bottom of spring 38' and the slide s1. The spring provides compressive loading of the stack S which assures reliable dispensing of the slides and prevents the tape 152 from being pulled out without drawing out the slides, due to the otherwise low friction between the tape and the slides.

Referring again to FIG. 11, it is seen that in this embodiment of the invention, the slides are withdrawn "sideways" from the container 154. I.e., the long side edge of the slides moves through the exit slot of the container, rather than the narrow end as in the previous three embodiments. This is advantageous because movement in that orientation obviates the need for an excessively long tape 152, the length of which thus need only be a little more than twice the width of a single slide, multiplied by the total number of slides in the stack S. The material from which the tape 152 is fabricated is not critical. However, it should be quite flexible and have a relatively slippery surface for smooth, easy unfolding. Thin plastic sheet materials are appropriate, among other possible tape materials.

Referring to FIGS. 11–13, it will be seen that a holder 44'—similar to holder 44 of FIG. 5 and having a base plate 46', a block 48' projecting upward from the base plate—has three upright arms, including two end arms 170 and a rear arm 172, best seen in FIG. 13. Since the displacement of the slides in this fourth embodiment is normal to that in the previously described embodiments, the rear arm 172 is desirable in order to provide support against the user's pulling force on the tape 154. The container 154 has three exterior sleeves arranged for receiving the three upright support arms 170, 172 of the holder 44'. The rear arm 172 is received between two rear sleeves 174, while each arm 170 slides into the open lower end of a corresponding end sleeve 176, as partly shown in FIGS. 11 and 12. The container 154 is fitted onto the holder 44' simply by sliding it down and causing the upright arms to mate into the corresponding support sleeves.

It is contemplated that the container 154 of this fourth embodiment may also be manufactured and sold as a complete, sealed unit prefilled with sterile or otherwise clean microscope slides.

In each of the four described embodiments of the invention, the material from which the container and associated elements may be made can be relatively inexpensive—particularly in those implementations which are intended to be disposable. Thus, virtually any sort of plastic, such as polystyrene, might be used, and the various elements to be joined could be joined by use of a suitable adhesive, by use of an organic solvent or by heat fusion. The holder or base may likewise be fabricated from plastic. However, especially if the container is factory filled and sealed—and intended to be disposable—the support base may be constructed from a more durable material, such as aluminum.

While several specific embodiments of the invention have been described and illustrated for purposes of clarity and example, it should be understood that many changes, substitutions and modifications to the described embodiments will be apparent to those possessed of ordinary skill in the art, without thereby departing from the scope and spirit of the invention as defined in the following claims.

What is claimed as novel is:

1. A dispenser for microscope slides, comprising:
   a container internally dimensioned to contain a stack of microscope slides between a top, a bottom, and a plurality of sides comprising a forward side, a rear side, a left side and a right side, said stack comprising a top end slide, a bottom end slide and at least one additional slide there between, in specified orientation within said container, an exit slot in said forward side positioned and dimensioned to permit selective passage of one said end slide there through, and
   an ejector mounted to said container for linear sliding displacement through an access slot in said rear side in alignment with said exit slot, said ejector having an inner portion internal to said container and an outer portion exterior thereto, said inner portion including a slide abutment engageable to one said end slide in a retracted position of the ejector for urging the end slide through said exit slot upon displacement of the ejector to a forward position;
   wherein said front side, said rear side, said right side and said bottom of said container are mutually joined in a rigid first enclosing structure, said left side and said top side are mutually joined in a rigid second enclosing structure, and said first enclosing structure and said second enclosing structure are hingedly connected at a junction comprising a bottom edge of said left side and a left edge of said bottom side.

2. The dispenser as recited in claim 1, wherein said ejector is a unitary structure.

3. The dispenser as recited in claim 1, wherein said access slot is defined in said top and said exit slot is near said top on said one of said sides, and further comprising spring means compressed between said stack of slides and said bottom for urging said stack against said top.

4. The dispenser of claim 3 wherein said ejector includes an interior plate carrying said slide abutment and a finger tab exterior to said container connected to said plate through said access slot.

5. The dispenser as recited in claim 1, wherein said access slot and said exit slot are adjacent to said bottom.

6. The dispenser as recited in claim 1, wherein at least one of said left and right sides is hinged for movement between an open and a closed position thereby to permit loading or removal of a stack of slides in an edgewise direction of the slides into or from said container.

7. The dispenser as recited in claim 1, further comprising retainer means for securing said first enclosing structure to said second enclosing structure in a closed condition of said container.

8. The dispenser as recited in claim 1, further comprising spacer means between said stack and said rear side, said ejector having a slide abutment end retractable from under said stack and into a space defined by said spacer means, thereby to permit engagement of said slide abutment end with a rear edge of a bottom end slide of said stack.

9. The dispenser of claim 8 wherein said spacer means are operative for urging all slides in said stack towards said front of the container.

10. The dispenser of claim 8 wherein said spacer means comprise spacer vanes extending longitudinally along the interior of said rear side of said container downward from a point in proximity to said top to said bottom, said container internally dimensioned for closely containing said stack between said spacer vanes and said front of the container, said vanes dimensioned and arranged for resilient flexing against said stack thereby to hold said stack against said front.

11. The dispenser as recited in claim 1, further comprising:
a holder having a base and one or more projections extending upward from said base; and at least one sleeve on said container positioned and dimensioned for closely receiving said one or more projections thereby to hold the container securely on said base.

12. The dispenser of claim 1 wherein said container and said ejector are made of polymer plastic material.

13. The dispenser of claim 1 wherein said container and said ejector are injection molded parts.

14. A disposable factory package for microscope slides with integral slide dispenser, comprising:
a container internally dimensioned to contain a stack of microscope slides between a top, a bottom, and a plurality of sides, said stack comprising a top end slide, a bottom end slide and at least one additional slide therebetween, in specified orientation within said container, an exit slot in one of said sides positioned and dimensioned to permit selective passage of one said end slide therethrough;
an ejector mounted to said container for linear sliding displacement in an access slot in said container, said ejector having an inner portion internal to said container and an outer portion exterior thereto, said inner portion including a slide abutment engageable to one said end slide in a retracted position of the ejector for urging the end slide through said exit slot upon displacement of the ejector to a forward position;
said container and said ejector being formed of thermoplastic material;
said container, said ejector and said stack of slides being in a substantially uncontaminated original state; and
an impermeable wrapper about said container for preserving said substantially uncontaminated original state.

15. The package of claim 14 wherein said impermeable wrapper is a thin film wrapped about said container.

16. The package of claim 15 wherein said thin film is a shrink wrap film.

17. The package of claim 14 wherein said container has a cover movable to an open position for loading microscope slides into the container, and closure means for securing said cover in a normally closed position.

18. The package of claim 17 wherein said closure means are operative for substantially securing said cover against subsequent reopening thereby to discourage refilling of the container with microscope slides.

19. The package of claim 18 wherein said closure means are mechanical closure means configured to make retentive snap engagement between said cover and a main portion of said housing.

20. A dispenser for microscope slides, comprising:
a container internally dimensioned to contain a stack of microscope slides between a top, a bottom, and a plurality of sides, said stack comprising a top end slide, a bottom end slide and at least one additional slide therebetween, an exit slot in one of said sides, said exit slot positioned and dimensioned to permit selective passage of a said end slide therethrough;
a tape folded and interlaced between the slides in said stack, said tape having a free end passing through said exit slot out of said container, such that said slides may be individually dispensed through said exit slot and removed from said container one at a time by pulling on said free end of said tape.

21. The dispenser of claim 20 further comprising spring means pressing on said stack of slides thereby to compress said tape between said slides thereby to increase frictional resistance to withdrawal of the tape from the stack when pulling on said free end.

22. The dispenser of claim 20 wherein said exit slot extends along a long dimension of the slides in the stack.

23. The dispenser of claim 20 wherein said tape is of thin relatively low friction synthetic material.

24. The dispenser of claim 20 wherein said exit slot is near said bottom of the container.

25. The dispenser of claim 20 further comprising a base configured for holding said container, and wherein said container has means removably engageable to portions of said base for stably supporting said container on an underlying surface.

26. The dispenser of claim 25 wherein said portions of said base comprise upright arms on said base and said means removably engageable comprise sleeves on said container adapted for closely receiving said arms when said container is set upon said base.

27. A dispenser for microscope slides for dispensing individual slides from a stack of slides having a top slide, a bottom slide and at least one intermediate slide, each slide in the stack having edges defining a plurality of sides of the stack, said dispenser comprising:
a container internally dimensioned to contain a stack of microscope slides between a top, a bottom, and a plurality of sides including a forward side, a rear side, a left side and a right side, an exit slot in one of said front side and said rear side for dispensing an end slide of said stack under the urging of a slidable ejector and a spring for urging said stack towards said exit slot, wherein one of said right side and said left side is movable to an open condition between said top and said bottom thereby to admit a stack of slides to be loaded in a sideways direction into said container between the spring and the exit slot.

28. The package of claim 27 further comprising closure means for securing said movable one of said sides in a normally closed position.

29. The package of claim 28 wherein said closure means are operative for substantially securing said movable one of said sides against subsequent reopening thereby to discourage refilling of the container with microscope slides.

30. A dispenser for microscope slides for dispensing individual slides from a stack of slides having a top slide, a bottom slide and at least one intermediate slide, each slide in the stack having edges defining a plurality of sides of the stack, said dispenser comprising:

a container internally dimensioned to contain a stack of microscope slides between a top, a bottom, and a plurality of sides including a forward side, a rear side, a left side and a right side, an exit slot in one of said sides for dispensing an end slide of said stack under the urging of a slidable ejector and a spring for urging said stack towards said exit slot, wherein one of said sides is movable to an open condition between said top and said bottom thereby to admit a stack of slides to be loaded in a sideways direction into said container between the spring and the exit slot; and an impermeable wrapper about said container for preserving said stack of slides in an uncontaminated state.

31. The package of claim 30 wherein said impermeable wrapper is a thin film wrapped about said container.

32. The package of claim 31 wherein said thin film is a shrink wrap film.

33. A dispenser for microscope slides, comprising:

a container internally dimensioned to contain a stack of microscope slides between a top, a bottom, and a plurality of sides comprising a forward side, a rear side, a left side and a right side, said stack comprising a top end slide, a bottom end slide and at least one additional slide there between, in specified orientation within said container, an exit slot in said forward side positioned and dimensioned to permit selective passage of one said end slide there through, and an ejector mounted to said container for linear sliding displacement through an access slot in said rear side in alignment with said exit slot, said ejector having an inner portion internal to said container and an outer portion exterior thereto, said inner portion including a slide abutment engageable to one said end slide in a retracted position of the ejector for urging the end slide through said exit slot upon displacement of the ejector to a forward position;

characterized in that said ejector is sized, dimensioned and operative for advancing at least one third of the length of said slide through said exit slot thereby to facilitate grasping and removal of the slide from the container.

34. A dispenser for microscope slides, comprising:

a container internally dimensioned to contain a stack of microscope slides between a top, a bottom, and a plurality of sides, said stack comprising a top end slide, a bottom end slide and at least one additional slide there between, in specified orientation within said container, an exit slot in one of said sides positioned and dimensioned to permit selective passage of one said end slide there through;

an ejector mounted to said container for linear sliding displacement through an access slot in said container, said ejector having an inner portion internal to said container and an outer portion exterior thereto, said inner portion including a slide abutment engageable to one said end slide in a retracted position of the ejector for urging the end slide through said exit slot upon displacement of the ejector to a forward position; and a holder having a base and one or more projections extending upward from said base; and at least one sleeve on said container positioned and dimensioned for closely receiving said one or more projections thereby to hold the container securely on said base.

* * * * *